(12) United States Patent
Pyo et al.

(10) Patent No.: US 11,752,450 B2
(45) Date of Patent: Sep. 12, 2023

(54) SELECTIVE EXTRACTION METHOD FOR NATURAL SUBSTANCES

(71) Applicant: D-NATURE CO., LTD., Seongnam-si (KR)

(72) Inventors: Jae Sung Pyo, Busan (KR); Min Woo Kim, Seoul (KR); Nam Kyu Park, Seoul (KR); Sung Mi Lee, Seongnam-si (KR)

(73) Assignee: D-NATURE CO., LTD., Seongnam-si (KR)

( * ) Notice: Subject to any disclaimer, the term of this patent is extended or adjusted under 35 U.S.C. 154(b) by 243 days.

(21) Appl. No.: 17/418,844

(22) PCT Filed: Jan. 2, 2020

(86) PCT No.: PCT/KR2020/000034
§ 371 (c)(1),
(2) Date: Jun. 27, 2021

(87) PCT Pub. No.: WO2020/141891
PCT Pub. Date: Jul. 9, 2020

(65) Prior Publication Data
US 2022/0073484 A1 Mar. 10, 2022

(30) Foreign Application Priority Data
Jan. 4, 2019 (KR) .................. 10-2019-0001031

(51) Int. Cl.
*B01D 11/02* (2006.01)
(52) U.S. Cl.
CPC ................. *B01D 11/0288* (2013.01)

(58) Field of Classification Search
CPC .................................................. B01D 11/0288
See application file for complete search history.

(56) References Cited

U.S. PATENT DOCUMENTS 5,804,206 A    9/1998  D'Amelio et al.

FOREIGN PATENT DOCUMENTS

| CN | 104840457 B | 12/2017 |
| KR | 10-2008-0011958 A | 2/2008 |
| KR | 10-2011-0077131 A | 7/2011 |
| KR | 10-2014-0125506 A | 10/2014 |

OTHER PUBLICATIONS

International Search Report for PCT/KR2020/000034 dated Apr. 10, 2020 from Korean Intellectual Property Office.
You, Pengtao et al., "Brevilin A induces apoptosis and autophagy of colon adenocarcinoma cell CT26 via mitochondrial pathway and PI3K/AKT/mTOR inactivation", Biomedicine & Pharmacotherapy, vol. 98, Feb. 2018, pp. 619-625.
Oh, Hyun Mi et al., "Inhibitory activity of 6-O-angeloylprenolin from Centipeda minima on farnesyl protein transferase", Arch Pharm Res., vol. 29, No. 1, Jan. 2006, pp. 64-66.

*Primary Examiner* — Sikarl A Witherspoon
(74) *Attorney, Agent, or Firm* — Revolution IP, PLLC

(57) ABSTRACT

An extraction method for nonpolar natural substances includes: a step of conducting extraction of natural raw materials to prepare a first liquid extract; a step of mixing the first liquid extract with a phase separation composition containing a lipophilic solubilizer and water, and conducting a second extraction; and a step of isolating the supernatant of the phase-separated solution to obtain non-polar natural substances.

8 Claims, 16 Drawing Sheets

Lipid-based Drug(fr.) Extract Systems

Solubility of surfactants

SELECTIVE EXTRACTION METHOD FOR NATURAL SUBSTANCES

TECHNICAL FIELD

The present invention relates to a method for selectively extracting a natural substance and, more particularly, to a method for selectively extracting a natural substance by using a dissolution-emulsion extraction (DEE) method, which refers to a technology of quickly dissolving, solubilizing, extracting and concentrating/isolating selective ingredients (non-polar/polar, poorly soluble/water-soluble, HLB) or substances out of natural products by inducing a physical emulsification.

BACKGROUND ART

An extraction is to isolate the ingredients contained in solid or liquid raw materials by dissolving the same with a solvent. As a general extraction method, a solid-liquid extraction method is used when raw materials are solid, and a liquid-liquid extraction method is used when raw materials are liquid.

The liquid-liquid extraction (LLE) method is to isolate a specific ingredient in a mixture from other ingredients by applying a solvent to a liquid mixture containing a solute.

In order to extract a non-polar substance in a natural substance, the liquid-liquid extraction method is generally used, but still has a problem in that non-polar solvents such as hexane, methane dichloride, ethyl acetate, etc., are very toxic during a liquid-liquid extraction, an extraction process is very inefficient and complicated due to a variously repeated extraction process and a drying process for removing the non-polar solvent, and production costs are high due to a long process, low extraction efficiency and a long process time.

For example, in the process for extracting brevilin A from *Centipeda minima*, a raw material is subjected to an extraction multiple times with methanol, and a liquid extract is mixed with hexane for a plurality of fractions, mixed with chloroform for a plurality of fractions, mixed with ethyl acetate for a plurality of fractions, and mixed with butyl alcohol so as to perform an extraction through a plurality of fractions, after which about 25 mg of brevilin A is extracted from 300 g of dry weight of *Centipeda minima* during the extraction, so that an extraction amount is very small with very low efficiency (Non-Patent Document 1).

As a result of experiments with other extraction methods, it was shown that a resin extraction shows a lower extraction efficiency and a saponification/unsaponification extraction shows no extraction or very low extraction efficiency.

Patent Document 1 discloses an extract of *Centipeda minima*, in which natural substances are extracted by a supercritical carbon dioxide extraction method, but this extraction method has a problem due to complicated conditions for use, a considerable amount of time for extraction, and a very low extraction efficiency.

Accordingly, it is necessary to develop a novel extraction method capable of easily extracting a non-polar natural substance with high efficiency from natural products, etc., so that the resulting extract may be easily used.

Patent Document 1: Chinese Registered Patent Publication 104840457 B
Non-Patent Document 1: Arch Pharm Res Vol 29, No 1, 64-66, 2006.

DISCLOSURE

Technical Problem

The embodiments of the present invention are to provide a method for extracting a natural substance by using a dissolution-emulsion extraction (DEE) method.

Technical Solution

According to one embodiment of the present invention, a method for selectively extracting a natural substance may include conducting an extraction of natural raw materials to prepare a primary liquid extract, mixing the primary liquid extract with a phase separation composition containing a lipophilic solubilizer and conducting a second extraction, and isolating the supernatant of the phase-separated solution to obtain non-polar natural substances In addition, according to one embodiment of the present invention, the supernatant of the phase-separated solution may include a lipophilic solubilizer and a non-polar natural substance.

Furthermore, according to one embodiment of the present invention, the non-polar natural substance may include brevilin A or a derivative thereof.

Moreover, according to one embodiment of the present invention, the non-polar natural substance may suppress or inhibit a JAK-STAT signaling process.

Besides, according to one embodiment of the present invention, the natural raw material may include any one or more selected from the group consisting of *Centipeda minima, Litsea glutinous, Arnica* genus plants and *Helenium* genus plants.

In addition, according to one embodiment of the present invention, 10 to 90 wt % of the phase-separated composition; and 10 to 90 wt % of the primary liquid extract may be mixed in the secondary extraction.

Furthermore, according to one embodiment of the present invention, the phase separation composition may further include 70 wt % or less of a nonionic surfactant.

According to another embodiment of the present invention, a method for selectively extracting a natural substance may include preparing a phase-separated liquid extract from a natural raw material by using a phase separation composition containing a lipophilic solubilizer, and isolating the supernatant of the phase-separated solution to obtain a non-polar natural substance.

Advantageous Effects

The embodiments of the present invention relate to a method for extracting a natural substance from raw materials such as wild flowers, etc., in which the non-polar natural substance can be extracted relatively easily with high efficiency by using a dissolution-emulsion extraction (DEE) method.

In addition, since a liquid-liquid extraction method using a toxic solvent is not used, steps such as drying, etc., can be omitted. As a solvent is harmless to the human body, an liquid extract containing a natural substance can be isolated and immediately used as a product without any other steps, and an absorption rate of the product can be increased due to micro-emulsification or limited micelle concentration.

BEST MODE

Figure 1:
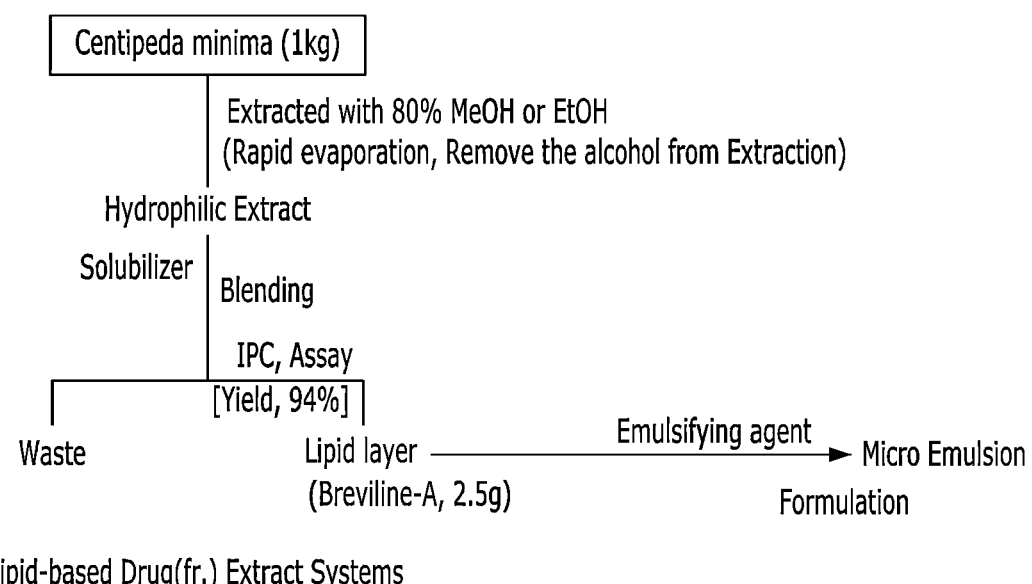
FIG. 1 is a view for explaining a method for selectively extracting a natural substance according to one embodiment of the present invention.

According to one embodiment of the present invention, a method for selectively extracting a natural substance may include conducting an extraction of natural raw materials to prepare a primary liquid extract, mixing the primary liquid extract with a phase separation composition containing a lipophilic solubilizer and conducting a second extraction, and isolating the supernatant of the phase-separated solution to obtain non-polar natural substances

MODE FOR INVENTION

Hereinafter, a method for extracting a non-polar natural substance according to embodiments of the present invention, a natural substance extracted according to the method, a use thereof, and the like will be described.

Prior to the description, the technical terms used herein are only for the purpose of referring to specific embodiments and are not intended to limit the present invention. As used herein, the singular forms also include the plural forms unless the phrases clearly indicate the opposite. In addition, as used herein, the meaning of "comprising" or "containing" specifies a particular characteristic, region, integer, step, operation, element or ingredient, and does not exclude the addition of other specific characteristic, region, integer, step, operation, element or ingredient.

In the present invention, the terms such as first, second, etc. are used to describe various components, and the terms are used only for the purpose of distinguishing one component from other components.

In addition, the terms used herein are used only for describing exemplary embodiments and are not intended to limit the present invention. The singular expressions include the plural expressions unless the context clearly indicates otherwise. In the present specification, the terms "comprising," "including," "having" or the like are intended to designate that the features, the numbers, the steps, the components, or combinations thereof are present, and are not to be understood as excluding the possibility that one or more other features, numbers, steps, components, or combinations thereof may be present or added.

Since the present invention may have various modifications and various forms, specific embodiments will be illustrated and described in detail below. However, this is not intended to limit the present invention to the specific disclosed forms, but it should be understood to include all modifications, equivalents and substitutes in the spirit and scope of the present invention.

Hereinafter, the present invention will be described in more detail.

In the present invention, the method for extracting a natural substance may refer to a dissolution-emulsion extraction (DEE) method.

The method for extracting a non-polar natural substance according to an embodiment of the present invention may include conducting an extraction of natural raw materials to prepare a primary liquid extract, mixing the primary liquid extract with a phase separation composition containing a lipophilic solubilizer, and isolating the supernatant of the phase-separated solution to obtain a non-polar natural substance.

According to the dissolution-emulsion extraction (DEE) method, a non-polar natural substance may be extracted by extracting the non-polar natural substance in a natural raw material, mixing with a phase separation composition, dissolving and emulsifying the resulting mixture, and carrying out a phase separation.

FIG. 1 is a view for explaining a method for selectively extracting a natural substance according to one embodiment of the present invention. FIG. 2B is a view for explaining a liquid-liquid extraction method, which is an existing extraction method of natural substances.

Figure 2:
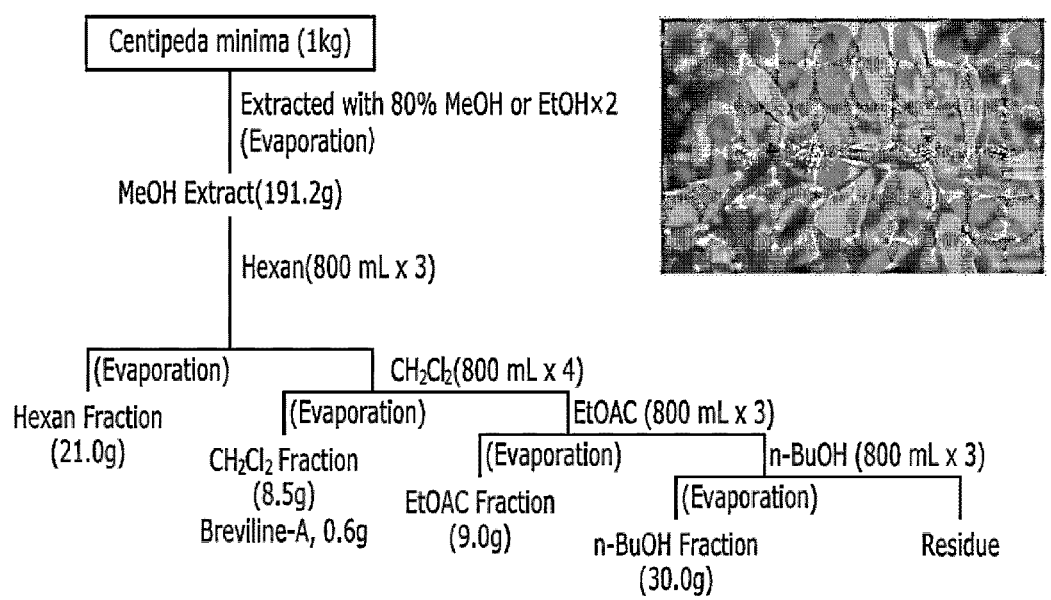
FIG. 2 is a view for explaining a liquid-liquid extraction method, which is an existing extraction method of natural substances.

FIG. 1 is a view for explaining a method for selectively extracting a natural substance according to one embodiment of the present invention. FIG. 2 is a view for explaining a liquid-liquid extraction method, which is an existing extraction method of natural substances.

As described above, in order to extract a non-polar substance in a natural substance, the liquid-liquid extraction method is generally used, but still has a problem in that non-polar solvents such as hexane, methane dichloride, ethyl acetate, etc., are very toxic during a liquid-liquid extraction, an extraction process is complicated, and extraction efficiency is low, thereby increasing production costs and a process time.

First, the natural raw material may be washed with water and dried. At this time, for example, the dried raw material may be pulverized to prepare a powder in order to increase an extraction rate of the natural substance.

According to one embodiment of the present invention, the natural raw material may include *Centipeda minima, Litsea glutinous, Arnica* genus plants and *Helenium* genus plants. The natural raw material used in the embodiments of the present invention, which is *Centipeda minima*, was purchased from the Goesan Herbal Organic Agricultural Cooperative Association (https://natural-herb.co.kr) as spreading sneezeweed (*Centipeda minima*, Yeongcheon).

In a number of documents, it has been found that brevilin A is contained in spreading sneezeweed (*Centipeda minima*), and in some documents, it has been reported that brevilin A is also contained in *Litsea glutinous*. Furthermore, some documents say that brevilin A is also partially contained in *Arnica* genus plants (*Arnica longifolia, Arctium lappa, Arnica chamissonis* subsp. *Foliosa, Arnica chamissonis* Less.) and *Helenium* genus plants (*Helenium autumnale* L, *Helenium alternifolium, Helenium pinnatifidum, Helenium vernale, Helenium brevifolium*, and *Helenium flexuosum*).

For example, the natural raw materials, in particular, *Centipeda minima*, may contain brevilin A or a derivative thereof. The non-polar natural substance extracted from *Centipeda minima* may contain brevilin A or various derivatives thereof.

The non-polar natural substance, which is an effective ingredient extracted from *Centipeda minima*, may suppress or inhibit a JAK-STAT signaling process.

Brevilin A may be a natural substance, which is widely known to suppress janus kinase activity (JAK) and inhibit STAT3 signaling in cancer cells (*PLoS One* 8 (5) (2013) e63697).

In other words, brevilin A may suppress and inhibit JAK-STAT signaling, thereby having an effect on autoimmune diseases such as rheumatoid arthritis, etc.

Throughout the literature, it has been reported that brevilin A is a major ingredient of *Centipeda minima* and a main focus has been concentrated on the studies on anti-cancer activity using the same, but there is no study on hair loss and hair growth.

For example, brevilin A may suppress or inhibit JAK-STAT signaling, thereby showing an effect on treatment of cold, itch, diabetes, corneitis, white coated tongue, occlusion of the nares, rhinitis, boil, asthma, sinusitis, dermatitis, malaria, chronic cough, removal of fever and whooping cough (pediatric disease) as well as autoimmune diseases including rheumatoid arthritis and cancer or tumors, and autoimmune diseases such as alopecia premature, traction alopecia, alopecia areata, alopecia neurotica, pityroid alopecia, trichotillomania, malignant alopecia, female pattern alopecia, male pattern alopecia, androgenic alopecia, telogen alopecia, tinea capitis, alopecia totalis, hypotrichosis, genetic hair loss, alopecia universalis or the like.

For example, the non-polar natural substance may include any one or more of the following compounds, which show a chemical structure of brevilin A and derivatives thereof (P. Wu et al./*Phytochemistry* 76 (2012) 133-140).

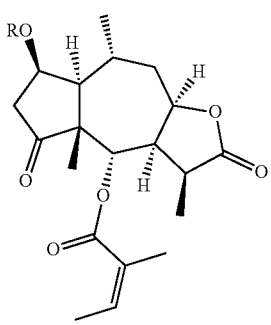

1 R = H
2 R = Et

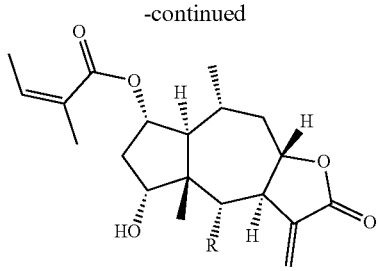

3 R = OH
4 R = H

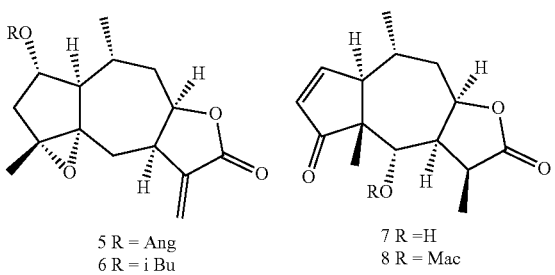

5 R = Ang
6 R = i Bu

7 R = H
8 R = Mac

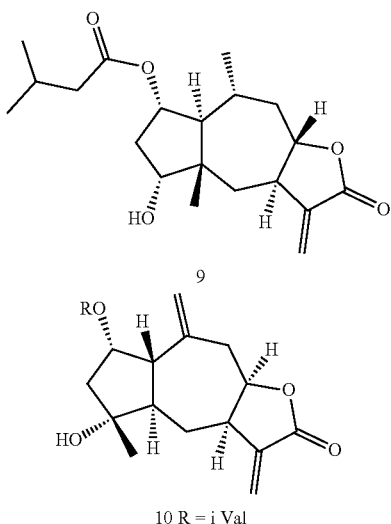

9

10 R = i Val
11 R = i Bu
12 R = Ang

13

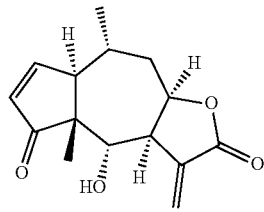

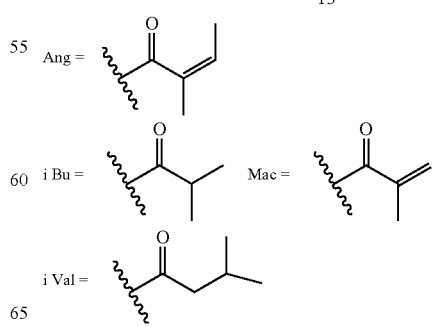

A primary liquid extract may be prepared by extracting a natural substance from a natural raw material.

As an extraction solvent, various solvents such as water, alcohol, etc., may be selected and used, and alcohol was used in the present invention. Preferably, methanol and ethanol may be used.

For example, an extraction may be performed by selecting and using any one of methods such as hot water extraction, cold extraction, reflux extraction, solvent extraction, steam distillation, ultrasonic extraction, elution, etc., and a conventional fractionation process may be further performed.

An extraction according to the embodiments of the present invention may be performed by immersing a natural raw material in alcohol and carrying out a hot water extraction at a temperature of 100° C. or higher for about one hour, and about 80% alcohol may be used as alcohol. For example, *Centipeda minima* may be used per se as a natural raw material, or may be used as a powder obtained by pulverizing the same.

For example, it may be possible to selectively perform a step of concentrating a primary liquid extract according to hot water extraction under reduced pressure and removing an alcohol ingredient therefrom. Although there is no difference in achieving the present invention even if a next step is immediately performed by using a primary liquid extract which has not undergone a concentration, it is preferable to remove an unnecessary alcohol ingredient in terms of clear phase separation and extraction efficiency.

As a result of analyzing 380 mg of the liquid extract obtained by performing a hot water extraction of 10 g of *Centipeda minima* hay with 400 mL of 80% ethanol, it was confirmed that the liquid extract contains 26 mg of brevilin A (0.26% content compared to the hay).

A phase separation composition may be added to the primary liquid extract and mixed.

Figure 3:
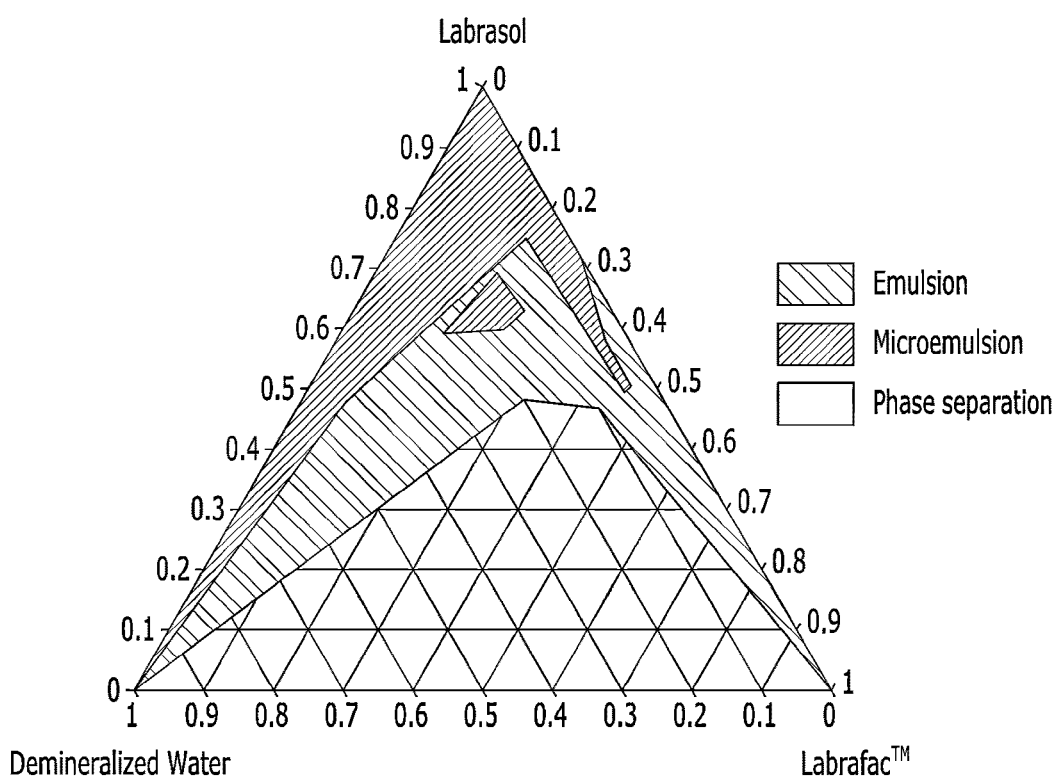
FIG. 3 is a view showing a three-phase state for explaining a composition ratio of a phase separation composition according to one embodiment of the present invention.
Figure 4:
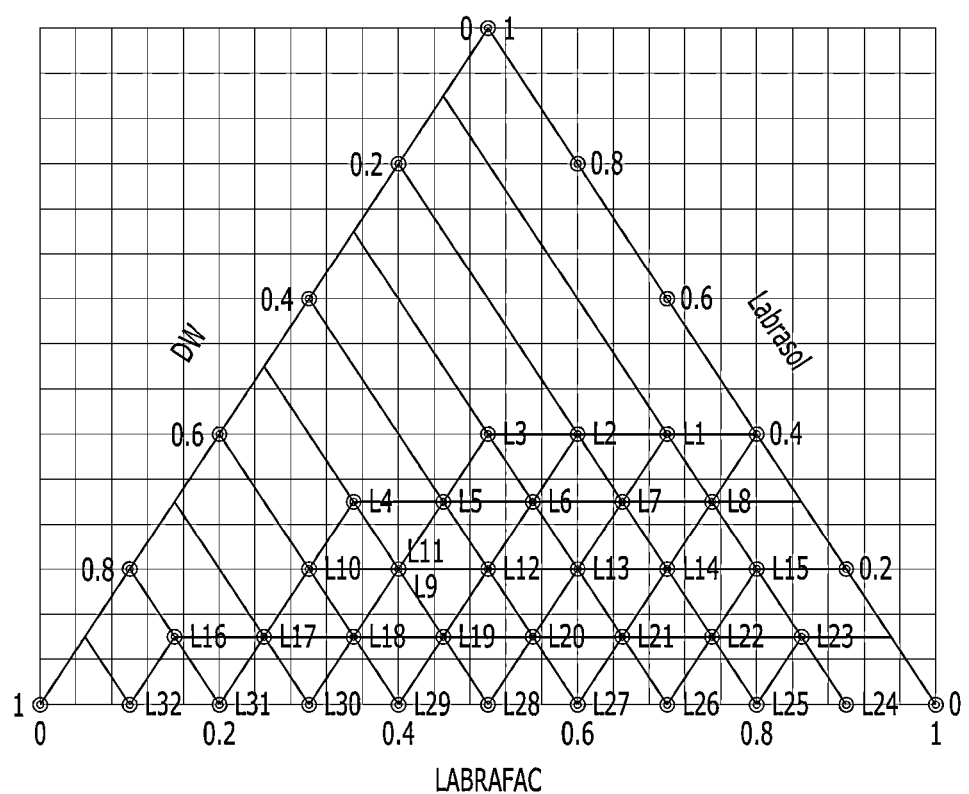
FIG. 4 is a view for explaining the composition of a phase separation composition according to embodiments of the present invention.
Figure 5:
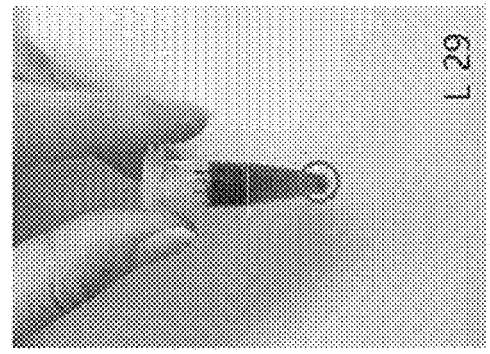
FIG. 5 is pictures for explaining a state in which a liquid extract is phase-separated by using a phase separation composition according to embodiments of the present invention.
Figure 5:
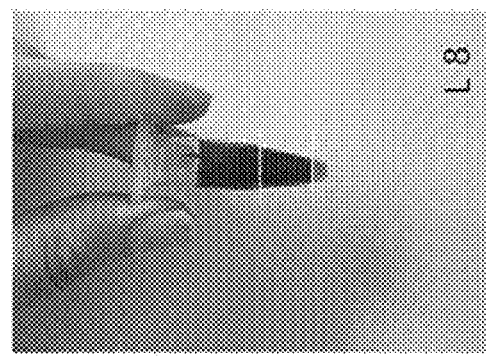
Figure 5:
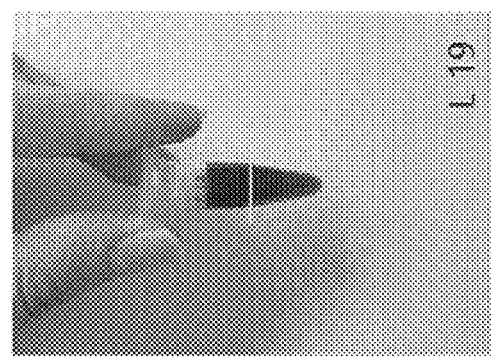
Figure 8:
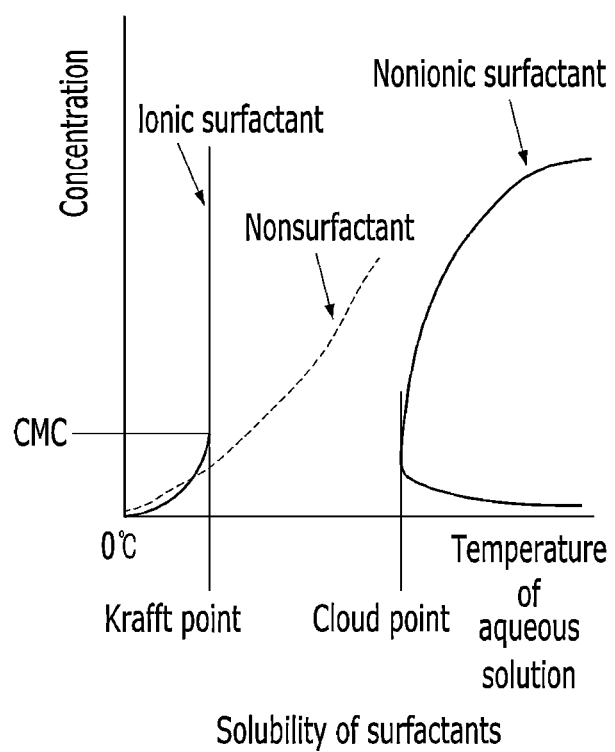
FIG. 8 is a view for explaining the behavior of a phase separation composition according to one embodiment of the present invention.

FIG. 3 is a three-phase state view for explaining a composition ratio of a phase separation composition according to one embodiment of the present invention. FIG. 4 is a view for explaining the composition of a phase separation composition according to embodiments of the present invention. FIG. 5 is pictures for explaining a state in which a liquid extract is phase-separated by using a phase separation composition according to embodiments of the present invention. FIG. 8 is a view for explaining the behavior of a phase separation composition according to one embodiment of the present invention.

The phase separation composition may include a lipophilic solubilizer. For example, the phase separation composition may be obtained by mixing 10 to 90 wt % of a lipophilic solubilizer; and 10 to 90 wt % of the primary liquid extract.

For example, the phase separation composition may further include a nonionic surfactant. The phase separation composition may include a nonionic surfactant in an amount of 60 wt % or less.

Referring to FIGS. 3 and 4, FIG. 3 shows a state which appears in a mixed solution according to the ingredients of the phase separation composition of the present invention, and indicates that a state of the solution changes into phase separation, micro-emulsion and emulsion according to a composition ratio of the lipophilic solubilizer, the nonionic surfactant and water. In FIG. 3, Labrafac may be one of the lipophilic solubilizers, and Labrasol may be one of the nonionic surfactants.

A composition ratio of the phase separation composition of the present invention was set according to a composition ratio of the region to be phase-separated based on a three-phase state view of FIG. 3. The phase separation compositions according to the embodiments of the present invention may exhibit a property in which layers are separated from each other without being mixed with a certain material for emulsification.

Thus, the non-polar natural substance contained in the natural raw material may be primarily extracted and then mixed with the phase separation composition, after which the lipophilic solubilizer and the non-polar natural substance are contained in one layer and the remaining water and other ingredients are contained in the other layer, so that a phase separation may occur.

The embodiments of the present invention relate to a method for selectively extracting a natural substance by using a dissolution-emulsion extraction (DEE) method, which refers to a technology of quickly dissolving, solubilizing, extracting and concentrating/separating selective ingredients (non-polar/polar, poorly soluble/water-soluble, HLB) or substances out of natural products by inducing a physical emulsification. By using this method, substances having any one property may be selectively extracted or removed vice versa from a mixture of non-polar/polar substances, poorly soluble/water soluble substances or substances having high/low HLB.

In the embodiments of the present invention, when the phase separation composition includes a nonionic surfactant, the mixing may be performed while raising a temperature for clearer phase separation in the step of mixing the phase separation composition. For example, the mixture in which the phase separation composition is mixed in the primary liquid extract may be stirred while maintaining a temperature of 30 to 50° C., preferably stirring while maintaining a temperature of 35 to 45° C.

FIG. 8 is a view for explaining the behavior of a phase separation composition according to one embodiment of the present invention. Referring to FIG. 8, when the primary liquid extract is mixed with the phase separation composition, brevilin A and derivatives thereof, which are a non-polar natural substance, may be extracted and dissolved in a nonionic surfactant or a lipophilic solubilizer. At this time, if additional high-speed mixing is performed, a surface area of the surfactant and the solubilizer in the mixture may increase, and most of the non-polar natural substances that are not extracted or dissolved may be dissolved, thus resulting in an instantaneous critical micelle concentration (CMC) state. At this time, when a temperature of the mixed solution increases to reach a cloud point, the solubility of the nonionic surfactant, unlike the ionic surfactant, may decrease as a temperature increases, and thus the phase separation of the mixed solution may more clearly occur.

In particular, a method of separating a phase by raising a temperature may advantageously act upon addition of a nonionic surfactant having a relatively high hydrophile-lipophile balance (HLB) value, for example, Labrasol, etc., having an HLB value of 12 or more.

For example, the nonionic surfactant may include any one or more selected from the group consisting of Labrasol, Crodex A-PA-(RB), Geleol, Gelot 64, Suppocire AS2X, Suppocire BML, Synperonic PE/F 127, Synperonic PE/L 44 and Tefose 63.

For example, the lipophilic solubilizer may include any one or more selected from the group consisting of BRIJ 010-SS-(RB), Capryol 90, Capryol PGMC, Gantrez ES-435, Gantrez S-97 BF, Gelucire 43/01, Gelucire 44/14, Gelucire 50/13, Gelucire 48/16, Labrafac CC, Labrafac Lipophile WL1349, Labrafac PG, Labrafil M 1944 CS, Labrafil M 2125 CS, Labrafil M 2130 CS, Lauroglycol 90, Lauroglycol FCC, Monosteol, Peceol, Pharmasolve, Plurol Oleique CC497, Span 20-LQ-(SG), Span 60-PA-(SG), upper Refined Oleic Acid-LQ-(JP), Super Refined Tween 80A-LQ-(MH), Surfadone LP-300, Transcutol HP, Transcutol P, TWEEN 60-SS-(SG), TWEEN 80 HP-LQ-(MH), TWEEN 80-LQ-(SG) and Vitamin E TPGS.

The supernatant of the phase-separated solution may be isolated to obtain a non-polar natural substance. The phase-separated solution was left alone for a certain period of time and then filtered by using a centrifuge.

Unlike the above, a method for selectively extracting a natural substance according to another embodiment of the present invention may include preparing a phase-separated liquid extract from a natural raw material by using a phase separation composition containing a lipophilic solubilizer and water, and isolating the supernatant of the phase-separated solution to obtain a non-polar natural substance.

In other words, in the above embodiment, the extraction and separation may be performed not by a two-step method of conducting an extraction of a natural raw material to prepare a primary liquid extract and then mixing with a phase separation composition to carry out a separation, but by a single-step method of mixing an extraction solvent and a phase separation composition in a natural raw material together to carry out an extraction. In this way, it is possible to shorten an extraction process step and time during extraction.

An emulsifying composition, which is in a range of micro-emulsion departing from a range of the phase separation composition, may be further mixed in a phase-separated layer containing a non-polar natural substance extracted according to the above methods, so as to prepare an emulsified product.

A product such as a natural substance extracted according to the embodiments of the present invention, a composition containing the same, and the like, may not use a liquid-liquid extraction method of using a toxic solvent, and thus steps such as drying, etc., can be omitted. As a solvent is harmless to the human body, an liquid extract containing a natural substance can be isolated and immediately used as a product without any other steps, and an absorption rate of the product can be increased due to micro-emulsification or limited micelle concentration (CMC).

In general, the use of surfactant may increase the absorption rate by increasing the solubility of the compound by using the CMC of the surfactant. In addition, the micro-emulsion may not only increase the solubility, but also reduce the size of the material to be absorbed, thereby increasing the absorption rate at an absorption site.

The products prepared as above may be prepared into a product such as hair tonic, hair conditioner, hair lotion, hair nourishing lotion, hair shampoo, hair conditioner, hair treatment, hair cream, hair nourishing cream, hair moisture cream, hair massage cream, hair wax, hair aerosol, hair pack, hair nourishing pack, hair soap, hair cleansing foam, hair oil, hair drying agent, hair preservative, hair dye, hair wave agent, hair bleach, hair gel, hair glaze, hair dressing, hair lacquer, hair moisturizer, hair mousse, hairspray, etc., and a formulation such as cream, gel, patch, spray, ointment, plaster, lotion, liniment, paste, cataplasma and the like as an external preparation for skin, and may be appropriately utilized as liquid, solid and gas phases.

The above products may be effective in ameliorating various diseases, to which the effect of brevilin A and derivatives thereof may be applied, thereby showing an effect on treatment of cold, itch, diabetes, corneitis, white coated tongue, occlusion of the nares, rhinitis, boil, asthma, sinusitis, dermatitis, malaria, chronic cough, removal of fever and whooping cough (pediatric disease) as well as autoimmune diseases including rheumatoid arthritis, lupus and cancer or tumors, and autoimmune diseases such as alopecia premature, traction alopecia, alopecia areata, alopecia neurotica, pityroid alopecia, trichotillomania, malignant alopecia, female pattern alopecia, male pattern alopecia, androgenic alopecia, telogen alopecia, tinea capitis, alopecia totalis, hypotrichosis, genetic hair loss, alopecia universalis or the like.

Hereinafter, the present invention will be described in more detail through Examples of the method for extracting non-polar natural substances of the present invention.

The extraction method of the present invention may be performed by extracting a natural raw material with hot water, mixing a phase separation composition in an liquid extract to carry out a phase separation, and separating some layer to obtain a non-polar natural substance.

Example

A natural raw material, which is *Centipeda minima*, was purchased from the Goesan Herbal Organic Agricultural Cooperative Association (https://natural-herb.co.kr) as spreading sneezeweed (*Centipeda minima*, Yeongcheon) and then washed and dried.

The 10 g of *Centipeda minima* hay was extracted with hot water by using 400 mL of 80% ethanol, so as to obtain a primary liquid extract. After that, the primary liquid extract was concentrated under reduced pressure to remove ethanol.

The primary liquid extract, which was concentrated under reduced pressure, and the phase separation composition were mixed according to the composition ratio shown in table 1 below, and stirred for 10 minutes. Following table 1 shows a description about the ratio of the compositions corresponding to the drawing of FIG. 4. L1 corresponds to Example 1 and L2 corresponds to Example 2, which are the same hereinafter.

After that, the resulting mixture was left alone 60 minutes and the phase-separated supernatant was isolated. The result of observing the phase-separated mixed solution is shown in FIG. 5, which is a picture showing the mixed solution of Examples 8, 19 and 29 in which phase separation occurs.

TABLE 1

| | Nonionic surfactant (wt %) - Labrasol | Lipophilic solubilizer (wt %) - Labrafac | Primary liquid extract (wt %) | Agitation method |
|---|---|---|---|---|
| Example 1 | 40 | 50 | 10 | Vortex mixer |
| Example 2 | 40 | 40 | 20 | Sonication |
| Example 3 | 40 | 30 | 30 | mechanical overhead stirrer |
| Example 4 | 30 | 20 | 50 | homogenizer |
| Example 5 | 30 | 30 | 40 | homogenizer |
| Example 6 | 30 | 40 | 30 | Circular inline mixer |
| Example 7 | 30 | 50 | 20 | Circular inline mixer |
| Example 8 | 30 | 60 | 10 | Circular inline mixer |

TABLE 1-continued

| | Nonionic surfactant (wt %) - Labrasol | Lipophilic solubilizer (wt %) - Labrafac | Primary liquid extract (wt %) | Agitation method |
|---|---|---|---|---|
| Example 9 | 20 | 30 | 50 | Circular inline mixer |
| Example 10 | 20 | 20 | 60 | Circular inline mixer |
| Example 11 | 20 | 30 | 50 | Circular inline mixer |
| Example 12 | 20 | 40 | 40 | Circular inline mixer |
| Example 13 | 20 | 50 | 30 | Circular inline mixer |
| Example 14 | 20 | 60 | 20 | Circular inline mixer |
| Example 15 | 20 | 70 | 10 | Circular inline mixer |
| Example 16 | 10 | 10 | 80 | Circular inline mixer |
| Example 17 | 10 | 20 | 70 | Circular inline mixer |
| Example 18 | 10 | 30 | 60 | Circular inline mixer |
| Example 19 | 10 | 40 | 50 | Circular inline mixer |
| Example 20 | 10 | 50 | 40 | Circular inline mixer |
| Example 21 | 10 | 60 | 30 | Circular inline mixer |
| Example 22 | 10 | [70] | 20 | Circular inline mixer |
| Example 23 | 10 | 80 | 10 | Circular inline mixer |
| Example 24 | 0 | 90 | 10 | Circular inline mixer |
| Example 25 | 0 | 80 | 20 | Circular inline mixer |
| Example 26 | 0 | 70 | 30 | Circular inline mixer |
| Example 27 | 0 | 60 | 40 | Circular inline mixer |
| Example 28 | 0 | 50 | 50 | Circular inline mixer |
| Example 29 | 0 | 40 | 60 | Circular inline mixer |
| Example 30 | 0 | 30 | 70 | Circular inline mixer |
| Example 31 | 0 | 20 | 80 | Circular inline mixer |
| Example 32 | 0 | 10 | 90 | Circular inline mixer |

The content of brevilin A in the supernatant was analyzed by HPLC (Water 2960 HPLC). HPLC analysis conditions are shown in table 2 below.

TABLE 2

| Item | Condition | |
|---|---|---|
| Column | SUPERSIL COLUMN ODS-I, 4.6 × 250 mm, 5 μm | |
| Mobile phase | Solvent A (45%) | Solvent B (55%) |
| | 0.1% formic acid in water | Methanol |
| Oven temp. | 40° C. | |
| Flow rate | 1 ml/min. | |
| Injection volume | 20 μℓ | |
| Run time | 30 min. | |
| Wave length | 224 nm | |

The 10 g of *Centipeda minima* hay was extracted with hot water by using 400 mL of 80% ethanol and 380 mg of the liquid extract was analyzed by HPLC, and it was confirmed that the liquid extract contains 26 mg of brevilin A (content of 0.26% compared to hay).

TABLE 3

| | Supernatant brevilin A content (mg) | Content ratio (%) of brevilin A in the isolated supernatant to the liquid extract |
|---|---|---|
| Example 1 | 15.37 | 59.12 |
| Example 2 | 11.25 | 43.27 |
| Example 3 | 10.15 | 39.04 |
| Example 4 | 20.98 | 80.69 |
| Example 5 | 8.72 | 33.54 |
| Example 6 | 10.91 | 41.96 |
| Example 7 | 12.83 | 49.35 |
| Example 8 | 9.97 | 38.35 |
| Example 9 | 15.71 | 60.42 |
| Example 10 | 9.17 | 35.27 |
| Example 11 | 12.83 | 49.35 |
| Example 12 | 13.53 | 52.04 |
| Example 13 | 12.95 | 49.81 |
| Example 14 | 20.87 | 80.27 |
| Example 15 | 12.14 | 46.69 |
| Example 16 | 14.02 | 53.92 |
| Example 17 | 13.00 | 50.00 |
| Example 18 | 16.01 | 61.58 |
| Example 19 | 13.58 | 52.23 |
| Example 20 | 13.82 | 53.15 |
| Example 21 | 12.71 | 48.88 |
| Example 22 | 14.55 | 55.96 |
| Example 23 | 18.71 | 71.96 |

TABLE 3-continued

|  | Supernatant brevilin A content (mg) | Content ratio (%) of brevilin A in the isolated supernatant to the liquid extract |
|---|---|---|
| Example 24 | 16.87 | 64.88 |
| Example 25 | 15.34 | 59.00 |
| Example 26 | 20.15 | 77.50 |
| Example 27 | 14.12 | 54.31 |
| Example 28 | 20.89 | 80.35 |
| Example 29 | 16.31 | 62.73 |
| Example 30 | 25.05 | 96.35 |
| Example 31 | 23.97 | 92.19 |
| Example 32 | 19.42 | 74.69 |

Comparative Example 1-LLE

A natural raw material, which is *Centipeda minima*, was purchased from the Goesan Herbal Organic Agricultural Cooperative Association (https://natural-herb.co.kr) as spreading sneezeweed (*Centipeda minima*, Yeongcheon) and then washed and dried.

The 10 g of *Centipeda minima* hay was extracted with hot water by using 250 mL of 80% ethanol, so as to obtain a primary liquid extract. The primary liquid extract was filtered and evaporated to dryness to obtain 0.82 g of extract.

The 10 ml of water (DW) and 20 ml of nucleic acid (cyclohexane) were mixed, stirred with a vortex mixer for one minute, and placed in a separating funnel, so as to isolate a nucleic acid layer. And the nucleic acid layer obtained by repeating the above process three times was concentrated and analyzed by HPLC.

The 20 mL of chloroform (MC) was mixed with an aqueous layer extract remaining after removing a nucleic acid fractional layer from above and was placed in a separating funnel to isolate a chloroform (MC) layer. And the chloroform (MC) layer obtained by repeating the above process 3 times was concentrated and analyzed by HPLC.

The 20 mL of ethyl acetate (EtAC) was mixed in an aqueous layer extract remaining after removing the chloroform (MC) fractional layer from the above and was placed in a separating funnel to isolate an ethyl acetate (EtAC) layer. And, the ethyl acetate (EtAC) layer obtained by repeating the above process 3 times was concentrated and analyzed by HPLC.

The 20 mL of butanol (n-BuOH) was mixed in an aqueous layer extract remaining after removing the ethyl acetate (EtAC) fractional layer from the above and was placed in a separating funnel to isolate a butanol (n-BuOH) layer. And, the butanol (n-BuOH) layer obtained by repeating the above process 3 times was concentrated and analyzed by HPLC.

An aqueous layer remaining after removing the butanol (n-BuOH) fractional layer from the above was concentrated and analyzed by HPLC.

Comparative Example 2-RESIN

A natural raw material, which is *Centipeda minima*, was purchased from the Goesan Herbal Organic Agricultural Cooperative Association (https://natural-herb.co.kr) as spreading sneezeweed (*Centipeda minima*, Yeongcheon) and then washed and dried.

The 10 g of *Centipeda minima* hay was extracted with hot water by using 250 mL of 80% ethanol, so as to obtain a primary liquid extract. The primary liquid extract was filtered, evaporated to dryness, mixed with 30 ml of water and 1 g of resin (HP-20), stirred with a vortex mixer at 250 rpm for one minute, and incubated for one hour. After that, ml of ethanol was mixed with resin remaining after isolating a primary supernatant through centrifugation (including water). A secondary supernatant was isolated (including ethanol) through centrifugation again. Each of the isolated supernatant was concentrated, resuspended in the same amount of ethanol, filtered by using a syringe filter, and analyzed by HPLC.

TABLE 4

|  | Brevilin A content (mg) | Content ratio (%) of brevilin A in the isolated supernatant to the liquid extract |
|---|---|---|
| Comparative Example 1 | 6.02 (Cyclohexane layer) | 23.00 |
|  | 8.16 (MC layer) | 31.17 |
|  | 5.12 (EtOAC layer) | 19.56 |
|  | 3.6 (n-BuOH layer) | 13.75 |
|  | 1.7 (Water layer) | 6.49 |
| Comparative Example 2 | — (Primary supernatant, aqueous layer) | — |
|  | 16.28 (Secondary supernatant, ethanol layer) | 62.62 |

Preparation Example

A supernatant (secondary liquid extract) isolated according to above Example 32 was concentrated (natural concentration at an elevated temperature) not to exceed 120% of the volume of the added lipophilic solubilizer, and 5 g of Labrasol was mixed as an emulsifying composition with the concentrated supernatant so as to prepare a micro-emulsion. Accordingly, a tonic preparation containing micro-emulsion 12 mg/mL, 8.5 mL, and yield of 95% was prepared. The above emulsion is a water base, not based on an organic solvent, and contains safe excipients and thus may be used per se as a product in various forms such as ointment, tonic, etc., without a separate additional process (Preparation Example 1).

Figure 6:
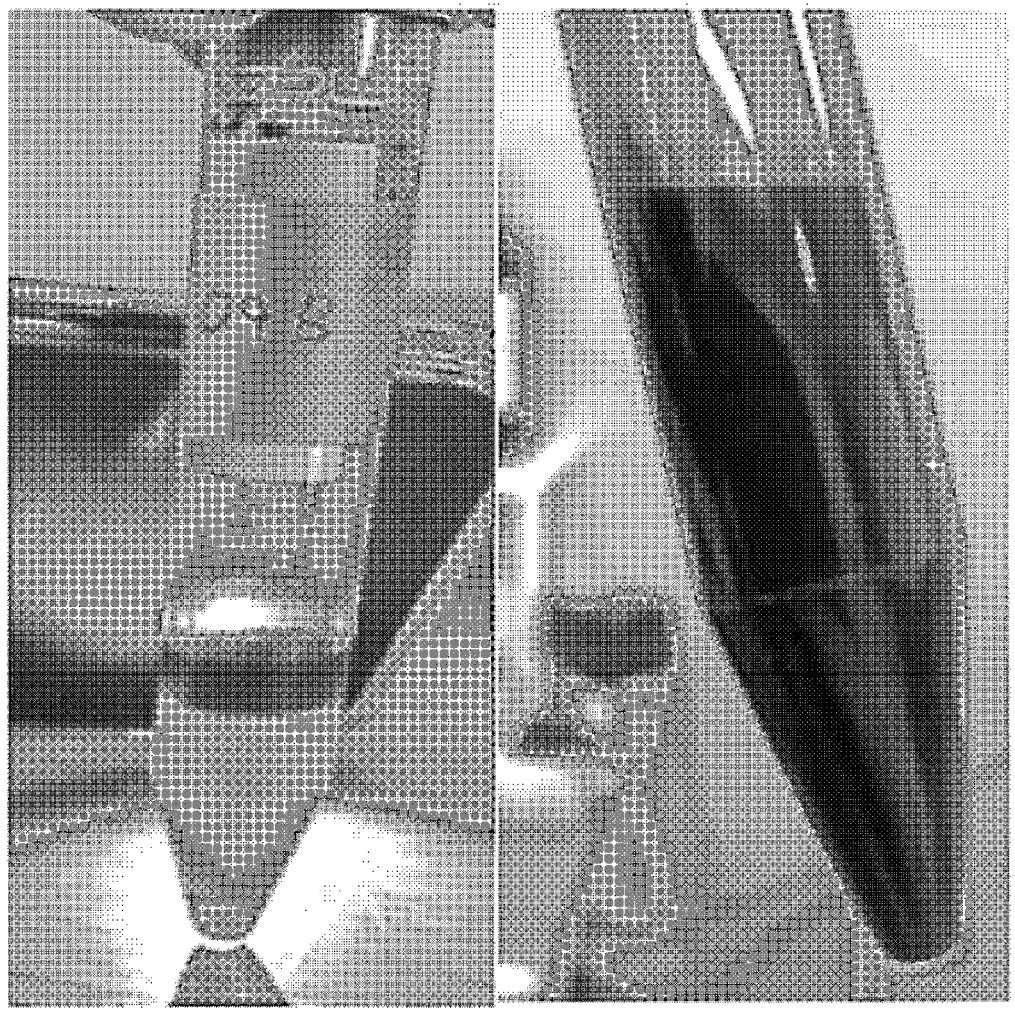
FIG. 6 is a picture (left) of a phase-separated state according to an embodiment of the present invention and is a picture (right) of a final prescription obtained by isolating the supernatant and further adding Labrasol for microemulsification.

FIG. 6 is a picture (left) of a phase-separated state according to an embodiment of the present invention and is a picture (right) of a final prescription obtained by isolating the supernatant and further adding Labrasol for micro-emulsification. A left picture of FIG. 6 shows the phase-separated primary liquid extract according to above Example 32, and a right picture of FIG. 6 shows a tonic preparation prepared according to above Preparation Example 1.

In contrast, 0.3 ml of Labrasol and 0.5 ml of Labrafac were mixed as an emulsifying composition in the supernatant (secondary liquid extract) isolated according to above Example 32 so as to carry out a micro-emulsification (Preparation Example 2). In contrast, 0.3 ml of Labrasol was mixed as an emulsifying composition in the supernatant (secondary liquid extract) isolated according to above Example 32 so as to carry out a micro-emulsification (Preparation Example 3). In contrast, 0.1 ml of Labrafac was mixed as an emulsifying composition in the supernatant (secondary liquid extract) isolated according to above Example 32 so as to carry out a micro-emulsification (Preparation Example 4). In contrast, 0.5 ml of Labrasol and 0.5 ml of Labrafac were mixed as an emulsifying composition in the supernatant (secondary liquid extract) isolated according to above Example 32 so as to carry out a micro-emulsification (Preparation Example 5). In contrast, 0.8 ml of Labrasol and 0.2 ml of Labrafac were mixed as an emulsifying composition so as to carry out a micro-emulsification (Preparation Example 6). The above emulsifying composition may depart from the scope of the phase separation composition of FIGS. 3 and 4, and may be appropriately applied in a range corresponding to the micro-emulsion of FIG. 3.

Figure 7:
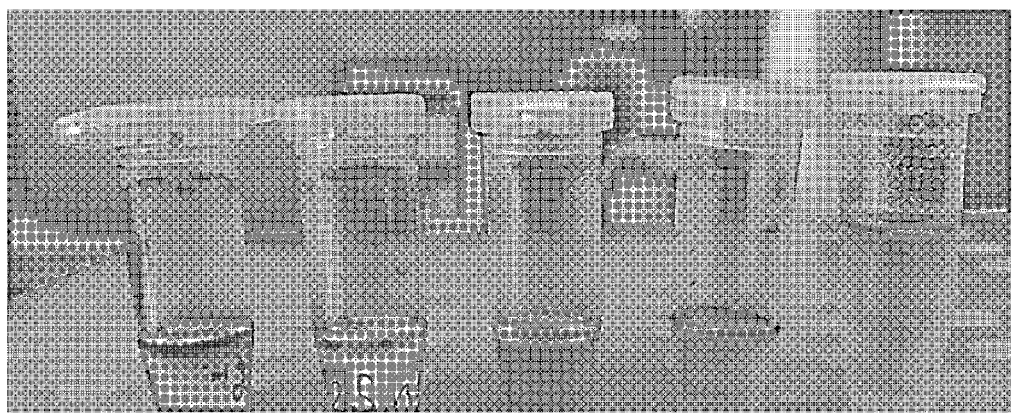
FIG. 7 is a picture for explaining a state in which a primary liquid extract according to an embodiment of the present invention is serially diluted and then phase-separated by using a phase separation composition.

FIG. 7 is a picture for explaining a state in which a primary liquid extract according to an embodiment of the present invention is serially diluted and then phase-separated by using a phase separation composition.

The above picture shows a state in which when performing a secondary extraction (dissolution emulsion extraction or lipid-based drug (fr.) extraction systems) from the primary liquid extract at various concentrations, braviline-A and derivatives thereof may be selectively concentrated, separated and extracted according to a lipophilic solubilizer regardless of a concentration and an amount with a performance suitable for extracting a trace amount.

The phase separation composition of the present invention may liquid extract all of the natural substances contained in the liquid extract regardless of the concentration of the non-polar natural substance to be extracted substantially contained in the primary liquid extract. In other words, the phase separation composition may be used to efficiently extract or remove a trace amount of substances. FIG. 7 shows the results of phase separation obtained by extracting the primary liquid extract according to Example 32, carrying out a serial dilution without concentration, and mixing the phase separation composition, respectively. In other words, although the concentration of the non-polar natural substance to be extracted is lowered, the same or similar phase-separated region is reduced, but it could be seen that a desired material may be separated by sufficient phase separation. Most of the pesticides remaining on fruits, vegetables, etc., may be non-polar (poorly soluble/lipophilic), may not be washed well, and may be deposited on the fibers of plants. The phase separation composition may be utilized to remove the pesticides remaining in the above plants.

Experimental Example

A change in the amount of hair loss and hair growth was measured as general men and women use a hair tonic prepared according to above Preparation Example 1 for a certain period of time. The hair tonic was used by applying directly to the scalp after clearly washing the hair with shampoo according to the user's level. Here, since it is rather difficult to accurately measure the amount of hair loss, the amount of hair loss was determined by the number of strands of hair filtered after showering, and the amount of hair growth was determined by the density of hair in the same area as measured by a hair diagnostic device.

Figure 9:
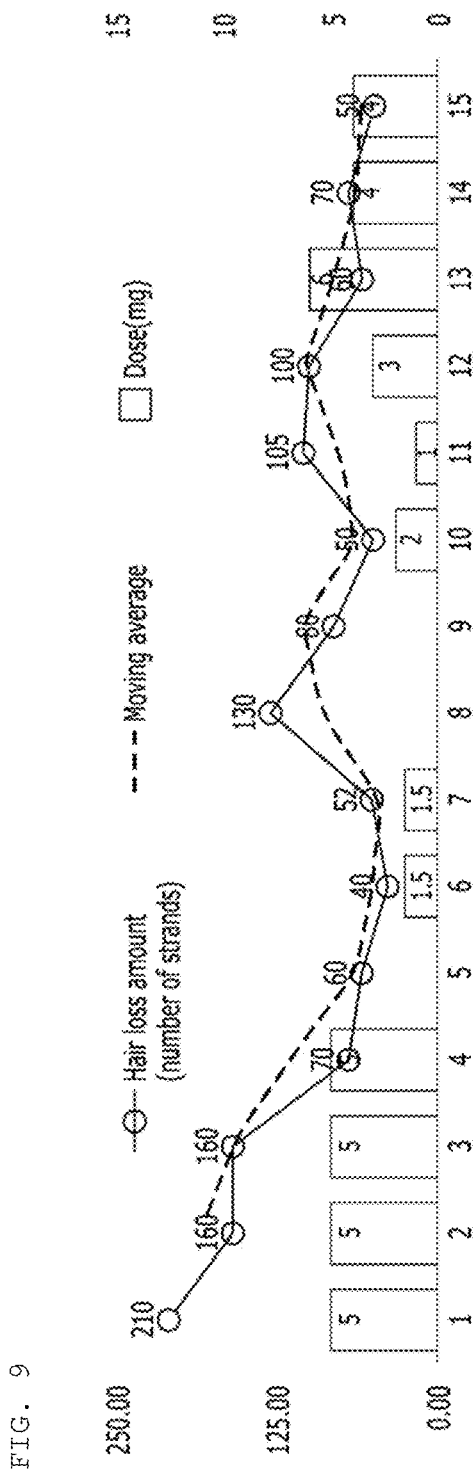
FIGS. 9 to 14 are views showing a change in the amount of hair loss and hair growth as a man uses a hair tonic prepared according to an embodiment of the present invention for 18 days.
Figure 15:
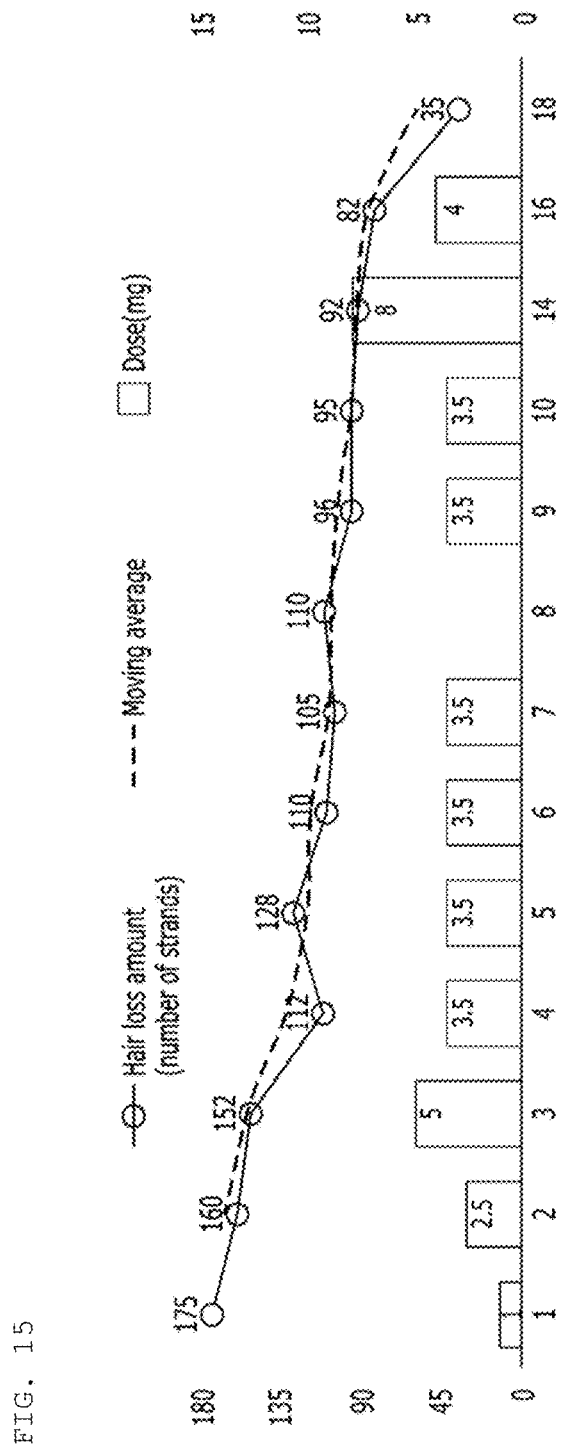
FIGS. 15 to 17 are views showing a change in the amount of hair loss and hair growth as a woman uses a hair tonic prepared according to an embodiment of the present invention for 18 days.
Figure 16:
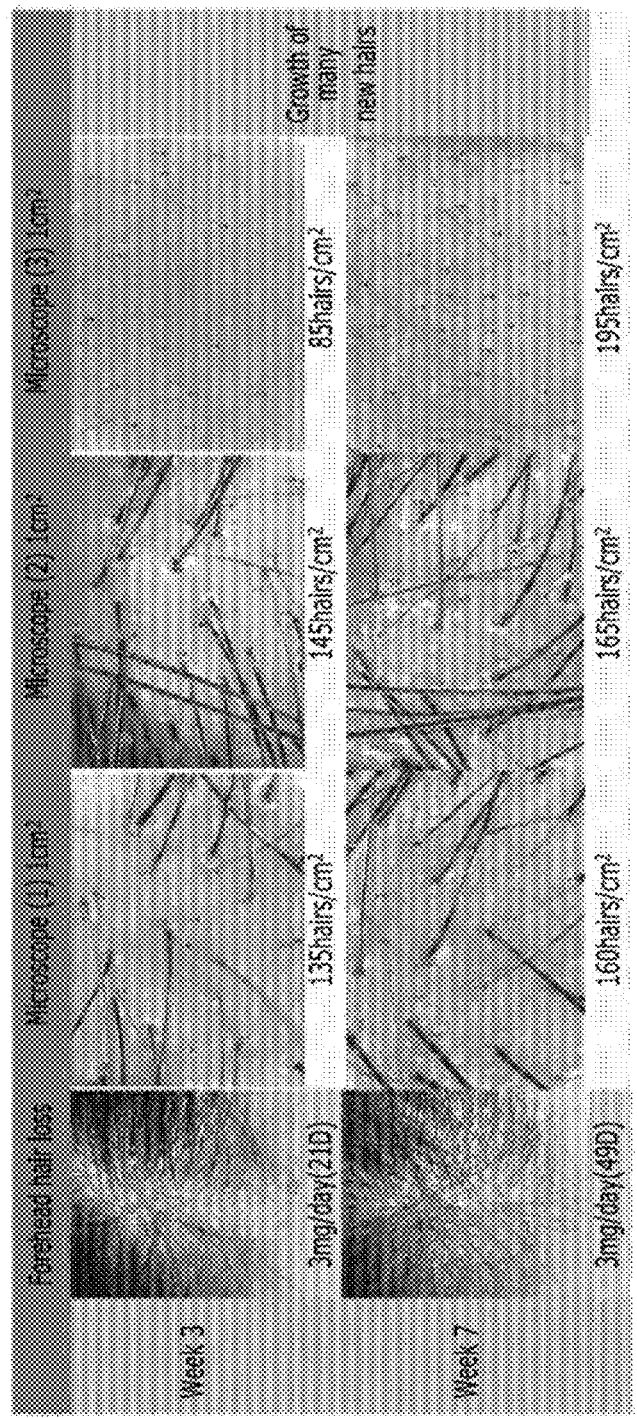
Figure 17:
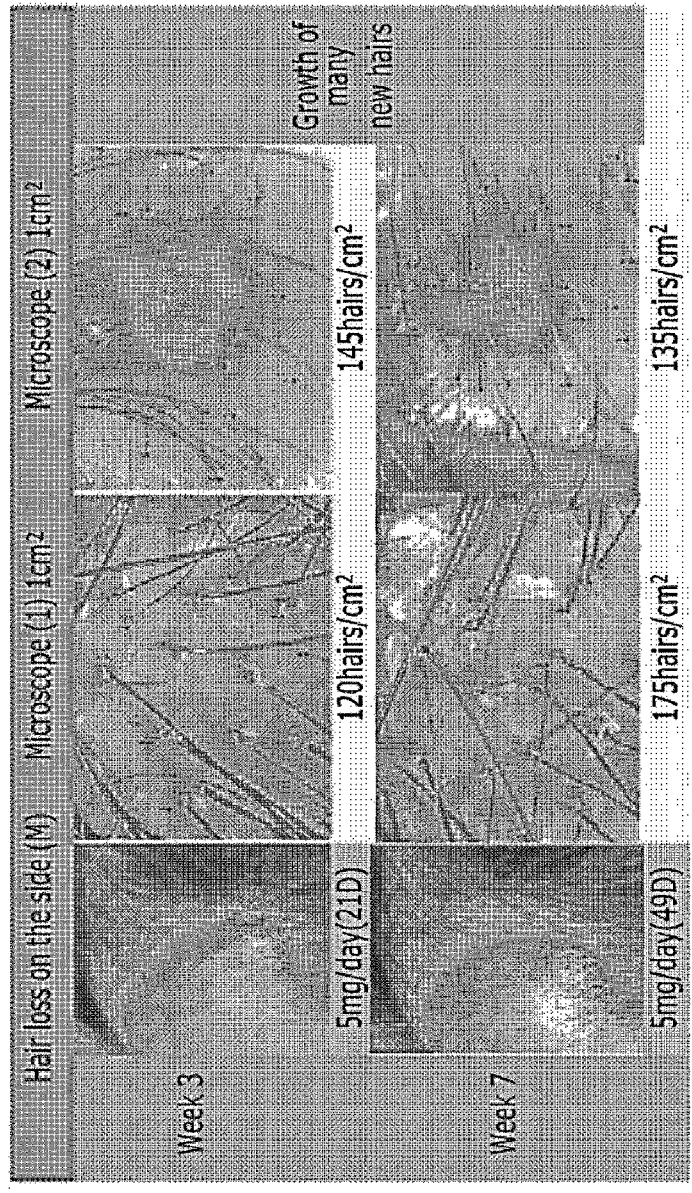

FIG. 9 is a graph showing a change in the amount of hair loss as a man uses a hair tonic prepared according to an embodiment of the present invention for 18 days. FIGS. 10 to 14 are views showing a change in the amount of hair loss and hair growth as a man uses a hair tonic prepared according to an embodiment of the present invention for 18 days. FIG. 15 is a graph showing a change in the amount of hair loss as a woman uses a hair tonic prepared according to an embodiment of the present invention for 18 days. FIGS. 16 and 17 are views showing a change in the amount of hair loss and hair growth as a woman uses a hair tonic prepared according to an embodiment of the present invention for 18 days.

Figure 10:
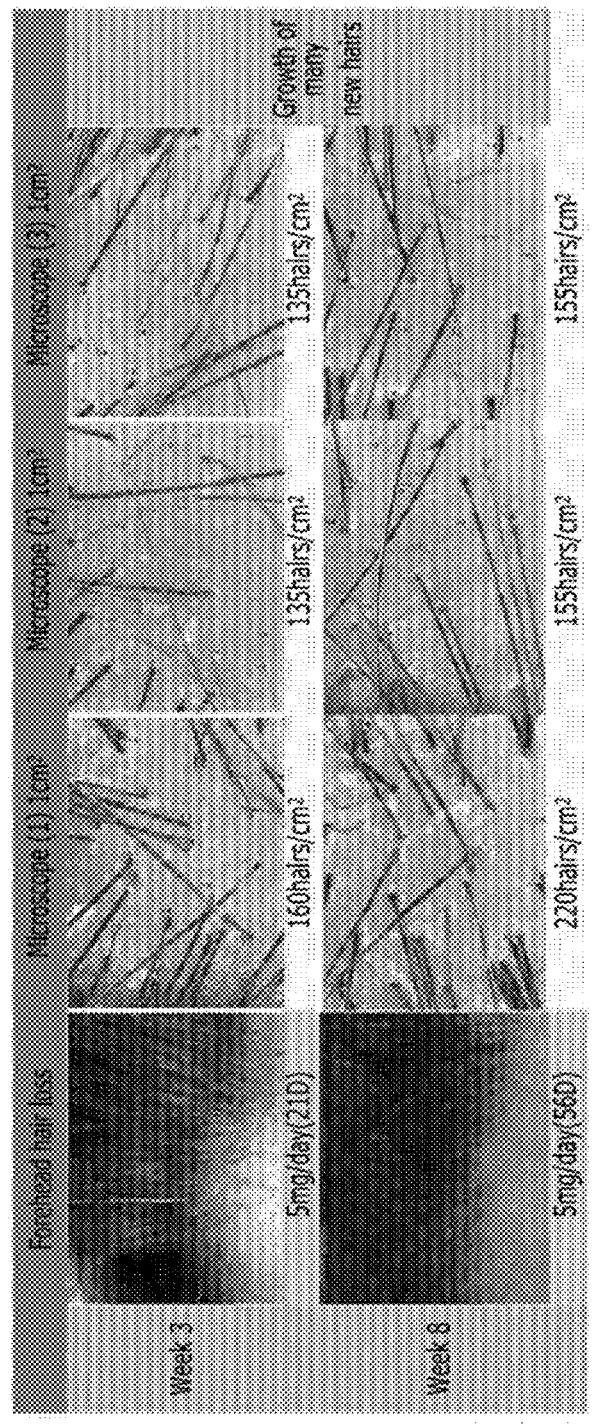
Figure 11:
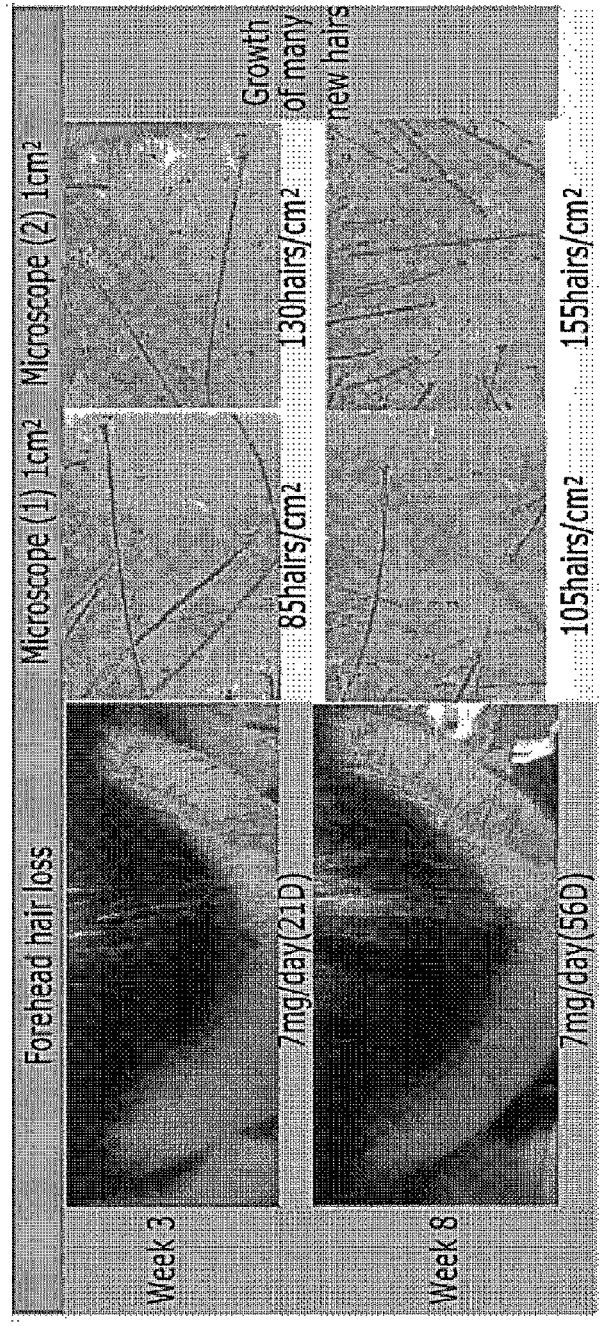
Figure 12:
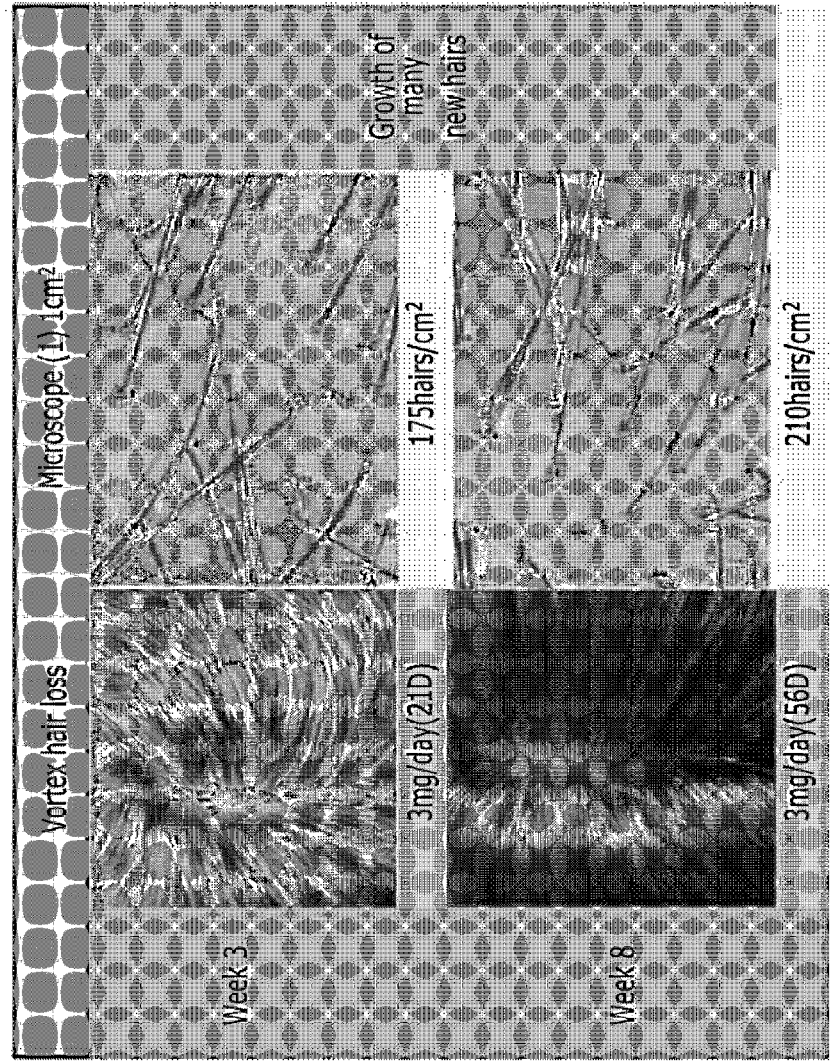
Figure 13:
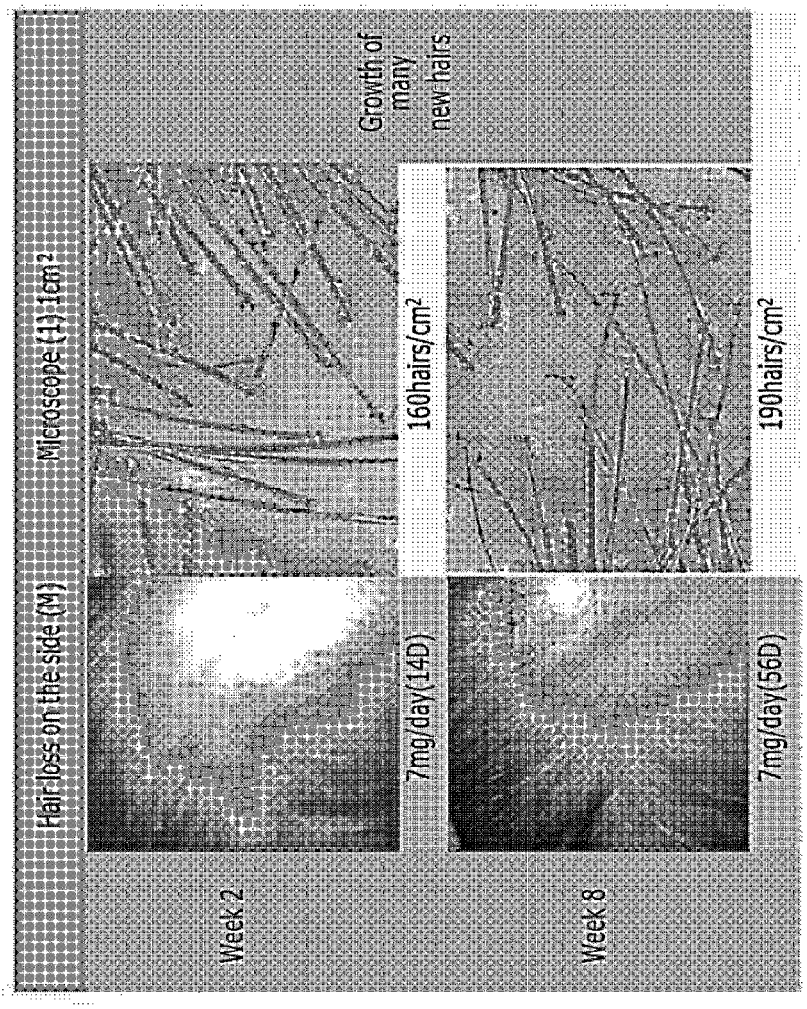
Figure 14:
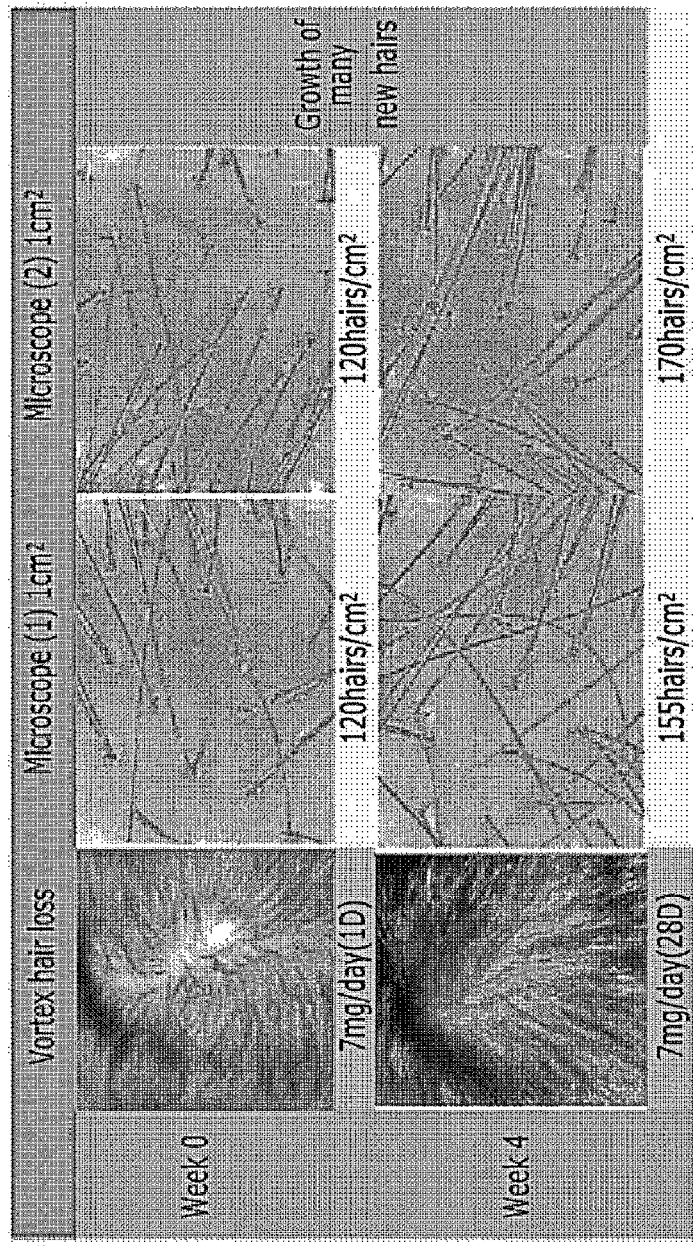

Referring to FIGS. 9 to 17, it could be seen that the amount of hair loss gradually decreases as the hair tonic is used in a certain amount, and it could be also seen that the amount of hair loss slightly increases as the use of the hair tonic is stopped during the experiment period. In particular, as a result of allowing the female subject to periodically use most of the hair tonic at a certain dose or more as shown in FIG. 10, it could be seen that the amount of hair loss is continuously reduced. It could be understood from FIGS. 10 to 14, 16 and 17 that the amount of hair growth is increased in both of the subjects, and the hair density is generally increased by about 15% or more and even up to 20% or more. Further, it could be confirmed that those subjects who used to show an amount of hair loss of 10 to 150 strands of hair show a stabilized amount of hair loss of 50 to 60 strands of hair after four weeks in terms of the harmonic average of the amount of hair loss.

As described above, the exemplary embodiments of the present invention have been described, but the present invention is not limited thereto, and it will be understood by those skilled in the art that various changes and modifications are made within the scope and concept of the following claims.

What is claimed is:

1. A method for extracting a non-polar natural substance, the method comprising:
   conducting an extraction of a natural raw material to prepare a primary liquid extract;
   mixing the primary liquid extract with a phase separation composition containing a lipophilic solubilizer, and conducting a second extraction; and
   isolating the supernatant of the phase-separated solution to obtain a non-polar natural substance.

2. The method of claim 1, wherein the supernatant of the phase-separated solution comprises the lipophilic solubilizer and the non-polar natural substance.

3. The method of claim 1, wherein the non-polar natural substance comprises brevilin A or a derivative thereof.

4. The method of claim 3, wherein the non-polar natural substance suppresses or inhibits a JAK-STAT signaling process.

5. The method of claim 1, wherein the natural raw material comprises any one or more selected from the group consisting of *Centipeda minima, Litsea glutinous, Arnica* genus plants and *Helenium* genus plants.

6. The method of claim 1, wherein 10 to 90 wt % of the phase separation composition; and 10 to 90 wt % of the primary liquid extract are mixed in the secondary extraction.

7. The method of claim 6, wherein the phase separation composition further comprises 60 wt % or less of a nonionic surfactant.

8. A method for extracting a non-polar natural substance, the method comprising:
   preparing a phase-separated liquid extract from a natural raw material by using a phase separation composition containing a lipophilic solubilizer; and isolating the supernatant of the phase-separated solution to obtain a non-polar natural substance.

\* \* \* \* \*